(12) United States Patent
Jensen

(10) Patent No.: US 7,330,754 B2
(45) Date of Patent: Feb. 12, 2008

(54) IMPLANTABLE MEDICAL DEVICE STREAM PROCESSOR

(75) Inventor: Steven L. Jensen, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 288 days.

(21) Appl. No.: 10/973,136

(22) Filed: Oct. 26, 2004

(65) Prior Publication Data

US 2005/0085859 A1 Apr. 21, 2005

Related U.S. Application Data

(63) Continuation of application No. 10/127,943, filed on Apr. 23, 2002, now Pat. No. 6,898,461.

(51) Int. Cl.
*A61N 1/08* (2006.01)

(52) U.S. Cl. .............................................. 607/2; 609/9

(58) Field of Classification Search .............. 607/2–23, 607/39–57
See application file for complete search history.

(56) References Cited

U.S. PATENT DOCUMENTS

| | | | |
|---|---|---|---|
| 4,481,580 A | 11/1984 | Bondurant et al. | |
| 5,144,568 A | 9/1992 | Glover | |
| 5,331,966 A | 7/1994 | Bennett et al. | |
| 5,708,595 A | 1/1998 | Connell | |
| 5,724,269 A | 3/1998 | Pedroni et al. | |
| 5,871,509 A | 2/1999 | Noren | |
| 5,995,868 A | 11/1999 | Dorfmeister et al. | |
| 6,016,449 A | 1/2000 | Fischell et al. | |
| 6,199,084 B1 | 3/2001 | Wiseman | |
| 6,223,083 B1 | 4/2001 | Rosar | |
| 6,230,049 B1 | 5/2001 | Fischell et al. | |
| 6,230,059 B1 | 5/2001 | Duffin | |
| 6,473,639 B1 | 10/2002 | Fischell et al. | |
| 6,602,202 B2 * | 8/2003 | John et al. ................... | 600/559 |
| 6,898,461 B2 * | 5/2005 | Jensen ........................... | 607/2 |

FOREIGN PATENT DOCUMENTS

| | | |
|---|---|---|
| EP | 0554208 A | 8/1993 |
| EP | 1050264 A | 11/2000 |
| WO | WO 9802209 A | 1/1998 |

OTHER PUBLICATIONS

Khailany et al., "Imagine: Media Processing With Streams", *IEEE Micro*, pp. 35-46 (Mar.-Apr. 2001).

* cited by examiner

*Primary Examiner*—Carl Layno
(74) *Attorney, Agent, or Firm*—John W. Albrecht

(57) ABSTRACT

A stream processor for an implantable medical device provides rapid computation using simple architecture and low power in which each input data sample is processed in parallel by a separate and independent central processing unit executing similar or identical kernel code consisting of the following elements. A housing contains a power source. A controller with memory coupled to the power source. A first physiological sensing apparatus and at least a second physiological sensing apparatus is coupled to the controller. A first stream processing element is coupled to the first physiological sensor and coupled to the controller. At least a second stream processing element is coupled to the second physiological sensor and coupled to the controller.

17 Claims, 14 Drawing Sheets

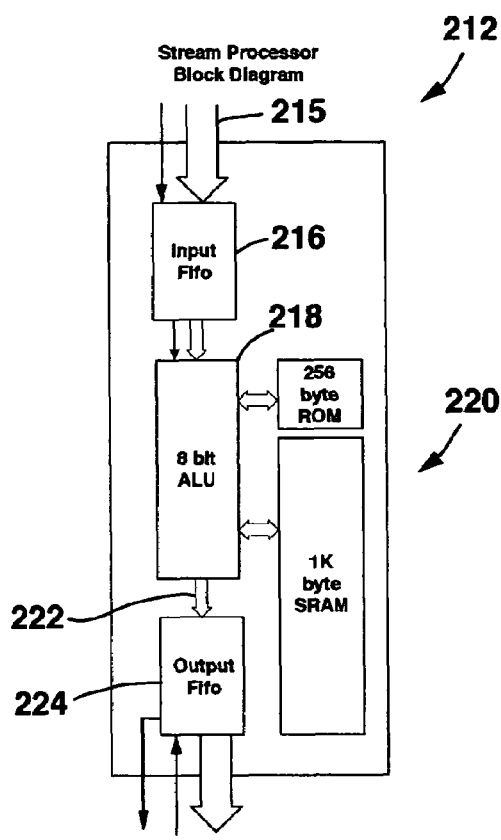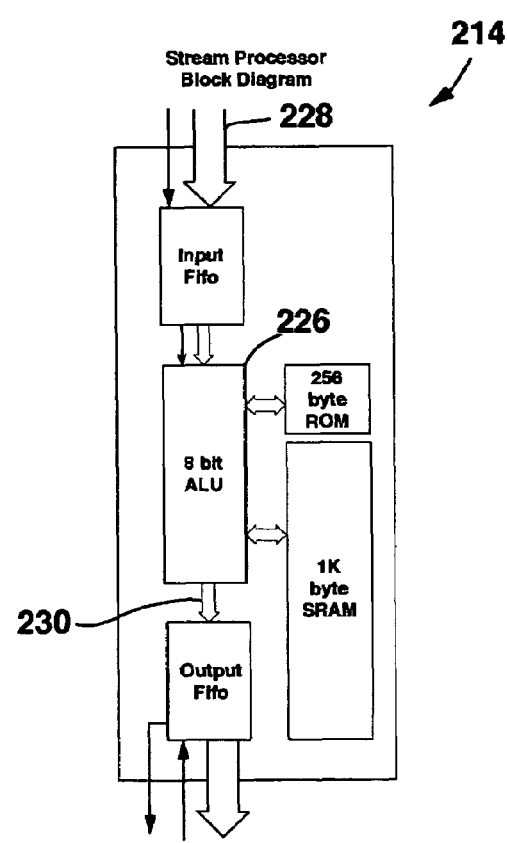
FIG. 21  FIG. 22

IMPLANTABLE MEDICAL DEVICE STREAM PROCESSOR

CROSS REFERENCE

This application is a continuation of application Ser. No. 10/127,943, filed Apr. 23, 2002, now granted as U.S. Pat. No. 6,898,461, that is hereby incorporated by reference.

FIELD OF THE INVENTION

This disclosure relates to a medical device and more particularly to implantable neurological electrical stimulators and implantable cardiac rhythm management devices.

BACKGROUND OF THE INVENTION

Modern implanted medical devices such as pacemakers, defibrillators, neurostimulators and the like are microcontroller-based and characterized by ultra-low power consumption (<100 uWatts), and relatively low processing demands. The typical lifetime for such devices is on the order of 3-10 years continuous operation using Lithium compound batteries with stored energy on the order of 2-8 Ampere-Hours, or nominal average current consumption in the range of 25 to 300 microamperes. For these applications, "performance" has not only a "clocks-per-instruction" component, but also a "power consumption" component. Typically the design goal becomes "adequate performance" for "minimum power". Throughout the medical device industry, these applications have become know as "ultra-low" power technologies and have begun to be of interest in the broader commercial sector with the explosion of portable "handheld" computing applications.

Remarkably, one of the primary approaches to achieving ultra-low power consumption in modern medical devices is to utilize techniques more commonly found in "high speed" supercomputers. By employing advanced, high-performance architectural mechanisms to improve the processing throughput of the micro-controller and subsequently retarding the processor clock, we are able to significantly reduce the overall power consumption of the processor. Ignoring static current drain issues, the dynamic current consumed by a CMOS processor is largely linear with respect to the processor clock rate and can be closely approximated as: I=CVF where I is the total dynamic current consumed, C is the circuit capacitance, V is the supply voltage for the processor and F is the clock frequency. Present ultra-low power circuit construction techniques minimize the capacitance and run at minimal supply voltages of 1.8 to 2 Volts. With any given design, it may be assumed that the C and V components of the design are minimal with present technologies, therefore reducing the total circuit complexity (and corresponding capacitance) and reducing the clock frequency are the only available design parameters left to the system architect. Furthermore, the dynamic current consumption is linearly proportional to the clock frequency.

Since reducing clock frequency is the primary approach for reducing current consumption, if we construct a very high-performance (in terms of instructions-per-clock) processor, we can simply slow the input clock to the point at which "adequate performance" is achieved, minimizing the power consumption variable while maintaining adequate processor bandwidth to handle the real-time processing needs.

One might note that the input clock could be maintained at high frequency, and simply have the processor run less frequently, however due to latency issues with starting/stopping the clock, and transistor level efficiencies, this method is less optimal. It has proven more effective to utilize as close to 100% of the processor bandwidth as possible, using a continuous, "slow" clock (on the order of 100 KHz for present generation devices).

The demand for increasingly complex features and more sophisticated signal processing in these devices is nearing a threshold at which current architectural methods will not yield adequate processing bandwidth. Specifically, the number of input signal sources is increasing, from 1 or 2 to 8-16 and more, along with the demand that each be processed in real-time using increasingly complex algorithms. An example of one such "complex" filtering algorithm employs a median filter in which a 256 sample median must be maintained for each of 8 separate input channels. The primary function of the filter is to return the median of the most recent 256 samples on a sample-by-sample basis, a task that requires a fairly sophisticated algorithm and which is generally impractical to implement in discrete logic. Similar applications are being considered for digitally sampled inputs up to 16 channels.

The current generation microcontroller is fabricated in 0.6 micron CMOS and consumes 30 microamps (uA) at a 100 KHz clock rate. The die size is approximately 300 mils per side and contains approximately 40,000 transistors (or approximately 10,000 gates). One obvious option for increasing performance without increasing power consumption is to use smaller geometry fabrication processes. As the channel length shrinks, the dynamic current decreases and transmission times also decrease yielding a fast circuit. However, the drawback for ultra-low power applications in shrinking geometries is the impact on static current drain. Using present technology (with non-insulating substrates), as the device size shrinks, the total static current drain (due to substrate losses and parasitic capacitances) increases. It is presently estimated that the lower limit for geometry based current consumption improvement in CMOS processors is approximately 0.15 microns, at which point the increase in static current drain begins to outweigh reduction in dynamic current and the total current consumption starts to increase. Therefore, it is likely that we can realistically improve the processor performance only by a factor of 4-5 using smaller geometry fabrication processes. This is clearly not sufficient to provide the order of magnitude performance improvement needed to handle the next generation applications.

Since geometry shrinking will only yield a 4-5 times improvement, we must consider more advanced architectural solutions if the next generation demands are to be met. Recent advances in public domain microprocessor architecture have focused on multiple issue super scalar techniques with deep pipelines, out-of-order instruction execution, complex non-blocking cache structures and sophisticated branch prediction schemes to improve the pure processing performance of the computing platform. Such techniques clearly improve the issue rate of the processor, but do so at great expense in terms of complexity and increased circuitry.

The increased complexity comes at a high cost in terms of device complexity at the transistor level. Beyond the simplest techniques, the cost quickly outgrows the benefit in terms of power consumption. Clearly, a quadratic increase in die area (and in the number of active components) quickly proves unacceptable for ultra-low power applications. A solution that seeks to minimize complexity with less circuitry is generally considered preferable.

The characteristics of biological signal data provided by multiple, independent sensors demand high-speed processing of large streams of low-precision integer data and generally share 3 key characteristics. First, the operations on one stream are largely independent of the others. Second, every stream element is read exactly once, resulting in poor cache performance. Third, they are computationally intensive, often performing 100-200 arithmetic operations for each element read from memory. The essential points are that 1) there is a very low level of data dependence (interdependence) and 2) there is significant course-grained thread level parallelism to be exploited. The recent developments in the area of chip-scale multiprocessors, in which multiple "simple" computing elements are arrayed on a single die to form a single-chip multiprocessor hold significant promise as a method for handling the processing needs of "stream" based applications.

General approaches to chip-scale multiprocessing have historically sought to leverage thread level parallelism in a general sense. The STAMPede project at Carnegie Mellon University has focused much attention to the issue of discovering thread level parallelism at the compiler level and providing a CMP architecture to support the execution of this code. Similarly, the Hydra and M-Machine projects also seek to exploit both fine and course grained thread level parallelism in a general-purpose sense. All three share a common architectural approach in which a single integrated circuit contains multiple copies of a simple processing element (ALU) with differing degrees of interconnectivity. Reminiscent of early RISC history, this approach seeks to utilize the additional circuit capacity by leveraging a simple hardware design and relying on compiler technology to efficiently exploit the multiple processing paths in the processor. Although these techniques are generally applicable to the implanted medical device architecture, the need for general processing does not exist when processing data streams. The application program (once loaded) will operate throughout the life of the device. Therefore, the process of "discovering" and exploiting thread level parallelism is not an issue for the medical device application. We can take advantage of this aspect to simplify the architecture.

In contrast to these methods, a stream-processor employs a co-processor approach in which a single (control) processor interfaces directly to the stream-processor through a simple interface. The stream-processor contains 8 "copies" of a simple ALU, which has been optimized for data processing algorithms. Also on-chip is an interface to independent memory banks, which are connected to each stream processor through a stream register file.

Each ALU executes a small program that is referred to as a 'kernel' in which the specific data/signal processing algorithm is implemented. This simple architecture holds promise for the next generation implantable device applications. For the foregoing reasons, there is a need for an implantable stream processor that provides high-bandwidth processing while retaining the ultra-low power characteristics demanded by the filtering application.

Several proposed medical device applications involve the use of increasingly sophisticated filtering techniques applied to continuously digitized input signals. One such technique employs a median filter. A median filter of size n is a method which, given a new sample, z, from a continuous digitized stream of samples, includes z with the preceding n-1 samples and returns the median value of the n total samples in the filter. For each successive z in the input stream, the median filter returns the median value for z plus the n-1 preceding values at the same rate as the input data.

Prototype median filtering methods have been based on variants of insertion-sort in which the new sample z is inserted into a sorted list of the preceding n samples and the "middle" value of the sorted list returned as the median. These methods generally take O(n) time and currently require the use of a non-implantable computer to implement. Present and proposed implanted device architectures are not suitable to this approach. An example of a median filter that uses a comparison algorithm is show in U.S. Pat. No. 5,144,568 "Fast Median Filter" by Glover (Sep. 1, 1992).

BRIEF SUMMARY OF THE INVENTION

A stream processor for an implantable medical is disclosed that provides rapid computation using simple architecture and low power in which each input data sample is processed in parallel by a separate and independent central processing unit executing similar or identical kernel code comprises the following elements. A housing contains a power source. A controller with memory coupled to the power source. A first physiological sensing apparatus and at least a second physiological sensing apparatus coupled to the controller. A first stream processing element coupled to the first physiological sensor and coupled to both the power source and the controller. At least a second stream processing element coupled to the second physiological sensor and coupled to both the power source and the controller.

BRIEF DESCRIPTION OF THE DRAWINGS

FIG. 21 shows a detailed block diagram of a single stream processor embodiment; and, FIG. 22 shows another detailed block diagram of a single stream processor embodiment.

DETAILED DESCRIPTION OF THE INVENTION

Figure 1:
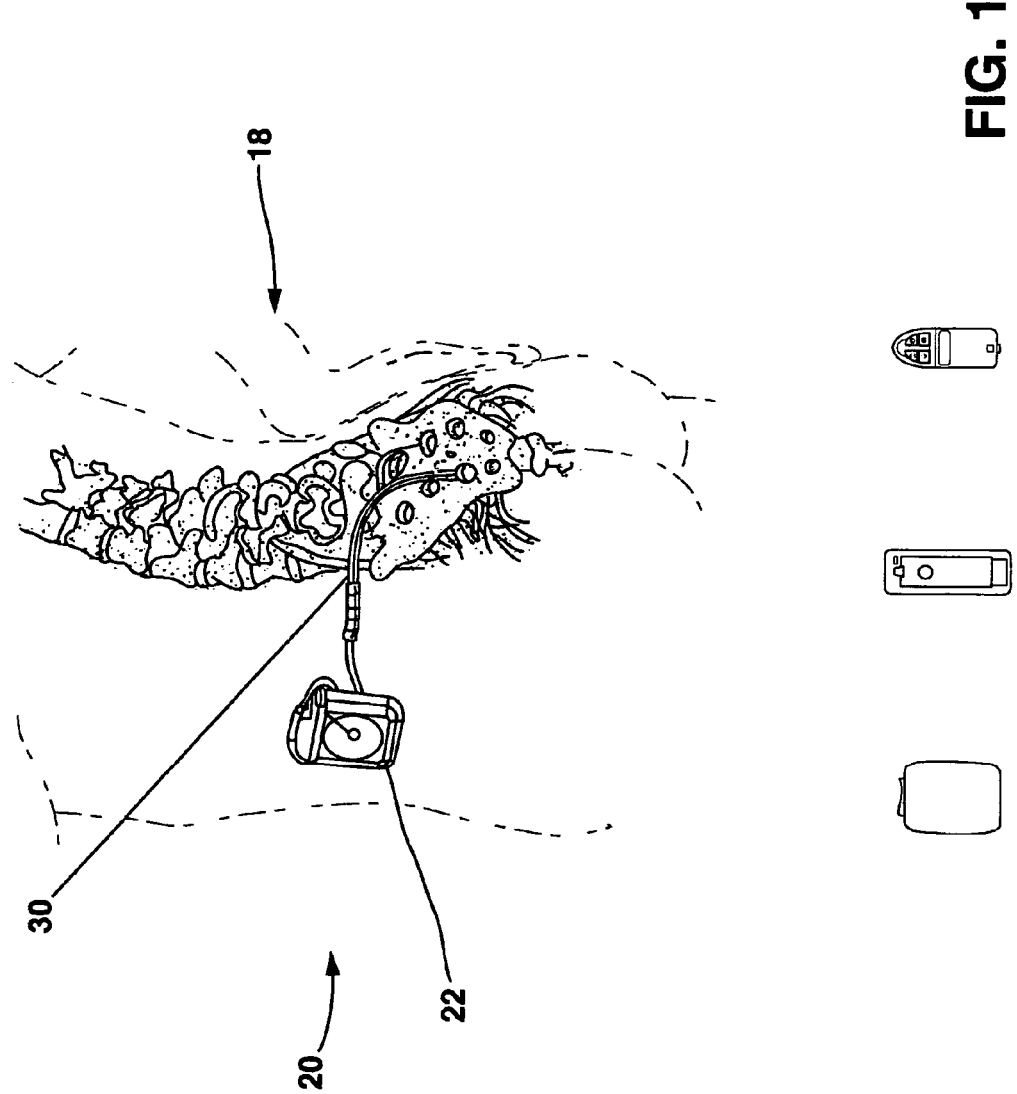
FIG. 1 shows a general environmental view for a neurostimulation system embodiment.
Figure 2:
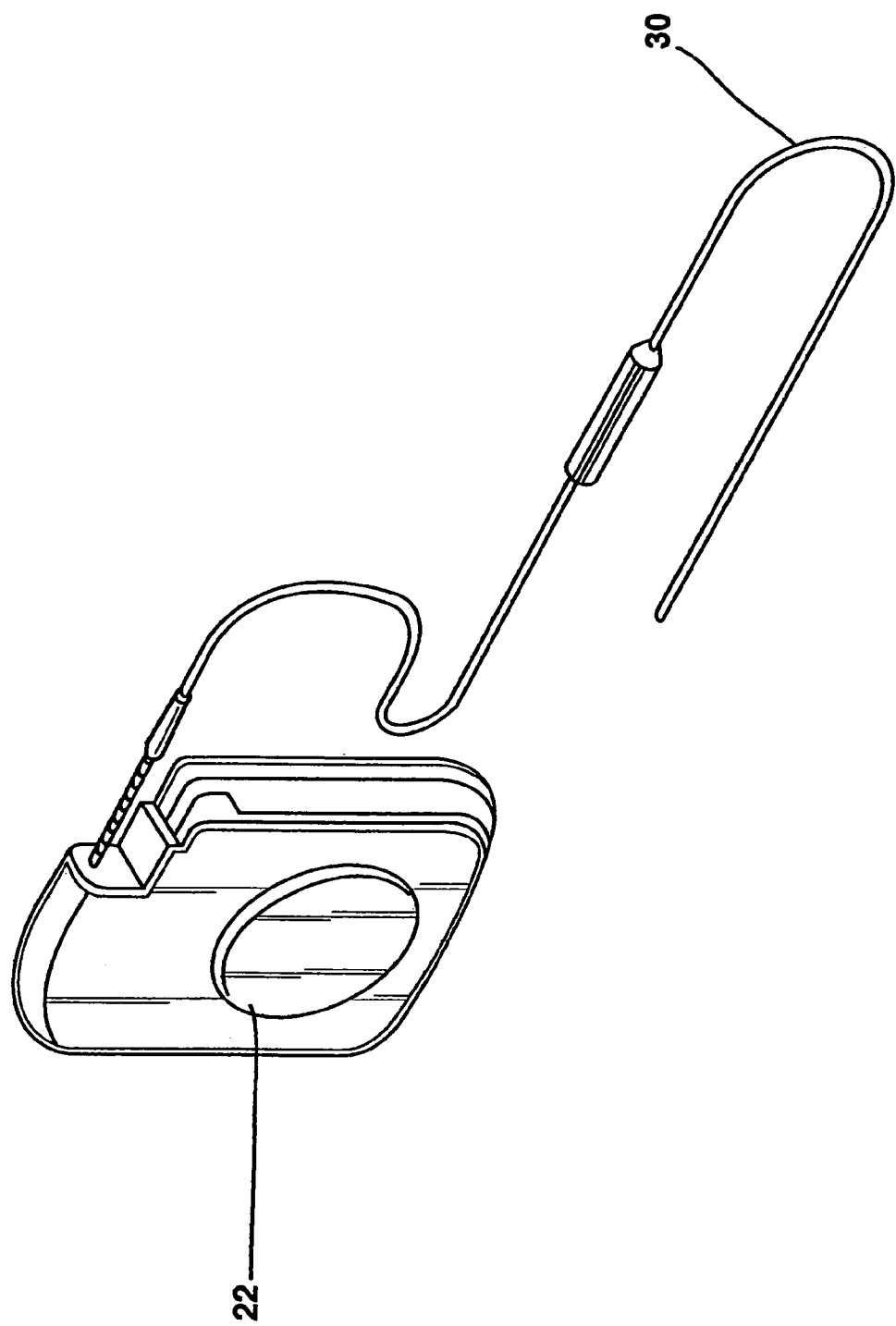
FIG. 2 shows a neurological stimulator embodiment.

FIG. 1 shows a general environmental view of an implantable neurostimulation system embodiment and FIG. 2 shows a neurostimulation system embodiment. Neurostimulation systems are used to treat conditions such as pain, movement disorders, pelvic floor disorders, gastroparesis, and a wide variety of other medical conditions. The neurostimulation system 20 includes a neurostimulator 22 such as an Itrel II® Model 7424 or an Itrel 3® Model 7425 available from Medtronic, Inc. in Minneapolis, Minn., a stimulation lead extension 24, and a stimulation lead 30. The neurostimulator 22 is typically implanted subcutaneously in the patient's body 18 at a location selected by the clinician. The stimulation lead 30 is typically fixed in place near the location selected by the clinician using a device such as the adjustable anchor. The implantable lead 30 can be configured as a neurological stimulation lead, a neurological sensing lead, and a combination of both as a neurological stimulation and sensing lead, a cardiac lead, and the like.

Figure 3:
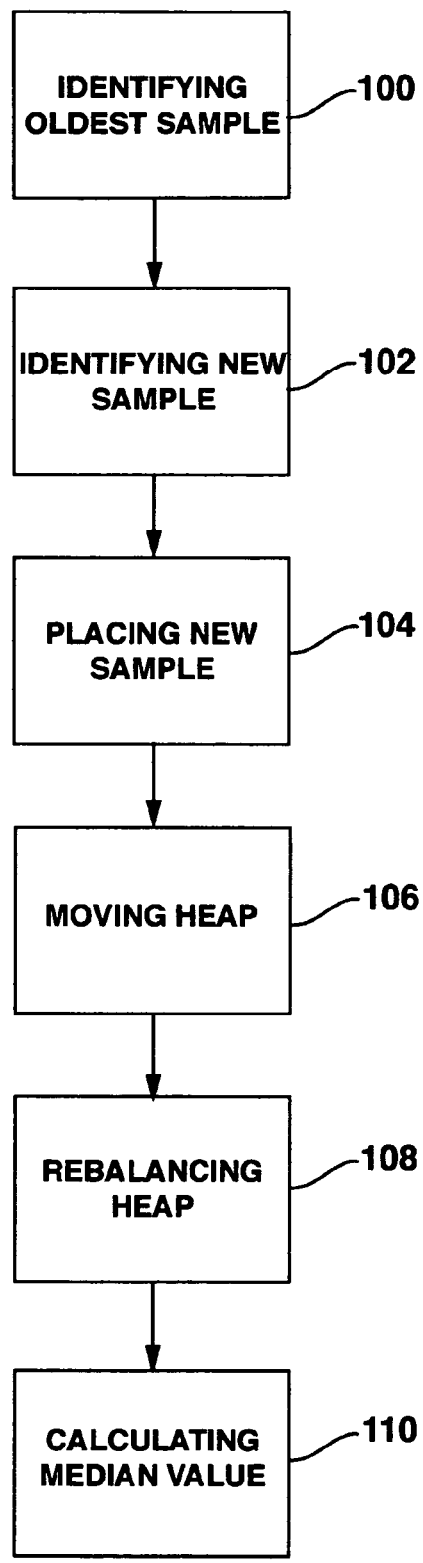
FIG. 3 shows a flow chart for a method of fast median filtering embodiment.

FIG. 3 shows a flow chart for a method of fast median filtering embodiment. A method for fast median filtering in an implantable medical device comprises the following elements. Receiving a new sample value into a buffer. Identifying an oldest sample 100 value location in a MIN-heap and a Max-heap 114. Identifying a new sample 102 value location in either the MIN-heap or the Max-heap 114 by comparing the new sample value to a median value. Placing the new sample 104 value into the oldest sample value location, if the MIN-heap or Max-heap 114 identified for the new sample value location is the same as the MIN-heap or MAX heap identified for the oldest sample value location. Moving 106 a MIN-heap top or Max-heap 114 top from the heap not containing the oldest value into the location of the oldest sample and placing the new sample into the location of the MIN-heap top or Max-heap 114 top moved from the heap not containing the oldest value, if the heap identified for the new sample is not the same as the heap identified for the oldest sample. Rebalancing 108 the Max-heap 114 so the Max-heap 114 top contains the highest value in the Max-heap 114 and rebalancing the MIN-heap so the MIN-heap top contains the lowest value in the MIN-heap. Calculating 110 the median value by averaging the MIN-heap top plus the Max-heap 114 top.

Figure 4:
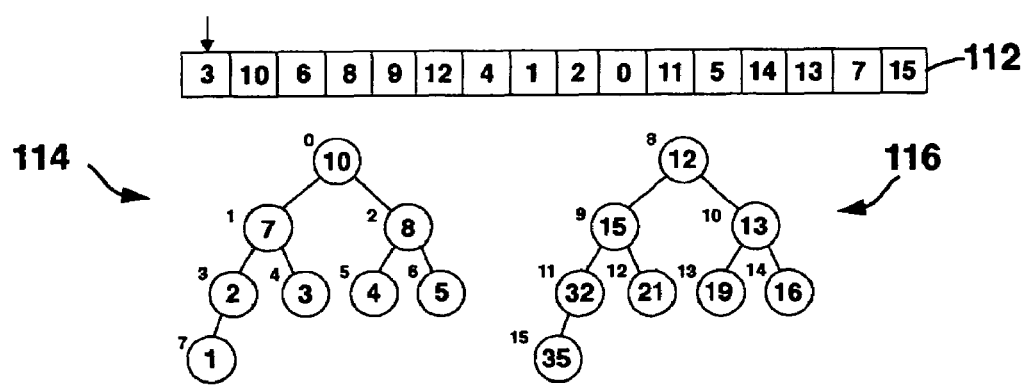
FIG. 4 shows a First-In-First-Out (FIFO) buffer, a Max-heap 114, and a MIN-heap embodiment.

FIG. 4 shows a First-In-First-Out (FIFO) buffer 112, a Max-heap 114, and a MIN-heap 116 embodiment. The method uses two binary heap structures, each containing n/2 of the stored samples in the filter to produce the median value of the n total samples in $$O(2 \log n/2)$$

time and has a small constant factor, yielding an efficient method which might be suitable for use by an implantable device. More specifically, The Max-heap 114 and MIN-heap 116 are arranged in a single array with the Max-heap 114 occupying locations 1 through n/2 samples and MIN-heap 116 occupying locations n/2+1 through n where n is the number of total samples.

Conceptually, the proposed method is straightforward: the n total samples in the filter are arranged in two binary heaps, a MAX heap 114 containing the smallest n/2 samples, and a MIN heap 116 containing the largest n/2 samples. The two heaps are arranged in a single array such that the MAX heap 114 occupies array locations 1 through n/2 and the MIN heap 116 occupies locations n/2+1 through n. Consistent with binary heaps generally, the MAX value of the smallest n/2 samples can be obtained in O(1) time and will be located at index 1. Similarly, the MIN value of the largest n/2 samples will be located at index n/2+1.

The median value is calculated by averaging the MIN-heap 116 top plus the Max-heap 114 top. The median value is simply computed as: (MAX+MIN)/2 which can be performed with a simple addition and a one bit shift in O(1) time. In addition to the standard heap property rules for the MIN and MAX heaps 114, 116, the median filter has two further properties which must be maintained: All the values stored in the MAX heap 114 must be less than or equal to the MIN value in the MIN heap 116. All the values stored in the MIN heap 116 must be greater than or equal to the MAX value stored in the MAX heap 114. These properties insure that the two "middle" values of the sorted input stream will exist as the MAX and MIN of the respective heaps.

The time required to calculate the median value is expressed by the equation, O(2 log n/2) where O is on the order of time and n is the number of total samples. In operation, the median filter takes a new value (z) as input, discards the "oldest" sample stored in the array and inserts the new value into either the MIN heap 116 or MAX heap 114 satisfying all heap properties and the median filter properties. Ignoring for the moment the problem of how to determine the "oldest" array element, the algorithm first deletes the "oldest" element from its respective heap and then inserts the new value into the proper heap. Since each heap contains n/2 elements, the respective operations (delete/insert) each take O(log n/2) time, for a total worst-case running time of O(2 log n/2). a4

A First-In-First-Out (FIFO) array 112 of n elements containing indexes that correspond to the Max-heap 114 and the MIN-heap 116 where n is the number of total samples addresses the problem of determining the "oldest" stored element. The separate circular FIFO array contains n pointers (actually indices to the heap array), and a corresponding "next" element pointer, which locates the oldest element in the FIFO array. In addition, the heap array elements are augmented with a "back" index, which locates the element in the FIFO array 112 corresponding to any given node. The back index is an Index (IDX) array of n elements containing back pointer indexes to corresponding First-In-First-Out (FIFO) elements where n is the number of total samples. This "back" index is used to update the FIFO indices whenever elements in the respective heaps must be swapped to maintain heap properties.

The median filter algorithm employs three arrays (note n is equivalent to FILTERSIZE). A FIFO array 112 of n elements containing indices to corresponding heap array elements. The FIFO element pointed to by the inext pointer contains the HEAP array index of the "oldest" element in the HEAP array. An IDX array of n elements containing "back pointer" indices to corresponding FIFO elements. Each HEAP array element contains a single pointer back to the FIFO array 112, used to update the FIFO pointers during Swap( ) operations. A HEAP array of n elements containing the most recent n sample values, organized into a size n/2 MAX heap and a size n/2 MIN heap.

To maintain the FIFO queue, a single pointer, inext always points to the next element in the queue. Also note, for implementation and efficiency reasons, all queues are indexed starting with 0 (zero) and ending with index n-1.

Table 1 below shows four necessary procedures that are introduced to handle frequent operations:

Left(i): Returns the index of the left child of i.
Right(i): Returns the index of the right child of i.
Parent(i): Returns the index of the parent of i.
Swap(i,j): Swaps the contents of HEAP and IDX array entries at i and j, and swaps the FIFO entries which point to these elements.

Note that indices are relative to zero, so the Left(i), Right(i) and Parent(i) are unusual with respect to other heap implementations.

TABLE 1

| Line | Item |
|------|------|
| 1 | LEFT(i) |
| 2 | return 2i+1 |
| 3 | RIGHT(i) |
| 4 | return 2i+2 |
| 5 | PARENT(i) |
| 6 | return (i−1)/2 |
| 7 | SWAP(i, j) |
| 8 | exchange HEAP[ i ] <--> HEAP[ j ] |

TABLE 1-continued

| Line | Item |
|------|------|
| 9 | exchange IDX[ i ] <--> IDX[ j ] |
| 10 | exchange FIFO[ IDX[ i ] ] <--> FIFO[ IDX[ j ] ] |

Prior to processing input data, the data structures must be initialized. The following procedure InitializeFilter( ) initializes the values in the three arrays and the value of the pointer inext. The values placed in the HEAP array are arbitrary, but must obey both the heap and median filter properties. For this project, the entire array is initialized to zeros, which satisfies all properties. Since all values in the heap following initialization will contain the same value, designation of the "oldest" is arbitrary. Referring to Table 2 below, accordingly, InitializeFilter initializes FIFO to point to node 0 as the oldest, node 1 as the next oldest, 2 the next, and so on. With this scheme, the back pointer array IDX can be initialized with the same values as FIFO. InitializeFilter will exit with inext set to 0.

TABLE 2

| Line | Item |
|------|------|
|  | InitializeFilter(FIFO, IDX, HEAP, inext, n) |
| 1 | FOR inext := n−1 TO 0 DO |
| 2 | FIFO[ inext ] := inext |
| 3 | IDX[ inext ] := inext |
| 4 | HEAP[ inext ] := 0 |

Referring to Table 3 below, following initialization, the median filter algorithm receiving a new sample value into a buffer by taking z, an input value and returning the median of the last n samples. This operation is handled by the MedianFilter procedure as follows:

TABLE 3

| Line | Item |
|------|------|
|  | MEDIANFILTER(FIFO, IDX, HEAP, inext, n, z) |
| 1 | i := FIFO[ inext ] |
| 2 | inext := (inext + 1) MODULO n |
| 3 | IF i < n/2    //index of "oldest" sample is in MAX heap |
| 4 | THEN    IF z > HEAP[ n/2 ] |
| 5 | THEN Swap( i , n/2) |
| 6 | HEAP[ n/2 ] := z |
| 7 | FixMinHeap( n/2 ) |
| 8 | ELSE HEAP[ i ] := z |
| 9 | FixMaxHeap( i ) |
| 10 | ELSE    IF z < HEAP[ 0 ] |
| 11 | THEN Swap( i , 0 ) |
| 12 | HEAP[ 0 ] := z |
| 13 | FixMaxHeap( 0 ) |
| 14 | ELSE HEAP[ i ] := z |
| 15 | FixMinHeap( i ) |
| 16 | return (HEAP[ 0 ] + HEAP[ n/2 ]) / 2 |

In lines 1-2, MedianFilter identifies an oldest sample value location in a MIN-heap and a Max-heap 114. The MedianFilter uses inext to obtain the index of the oldest node in the heap array from FIFO and then updates inext in a circular fashion. The "oldest" node is the one that will be discarded, creating a "hole" to place the new sample, z. A new sample value location is identified in either the MIN-heap 116 or the Max-heap 114 by comparing the new sample value to a median value. The new sample value is placed into the oldest sample value location, if the MIN-heap 116 or Max-heap 114 identified for the new sample value location is the same as the MIN-heap 116 or MAX heap 114 identified for the oldest sample value location.

At line three, the index is checked to see if the "hole" is in the MAX heap 114 or MIN heap 116. If the index is less than n/2, the hole is in the MAX heap 114. At line 4, the oldest node (hole) is in the MAX heap 114, and the value z is compared to the minimum value from the MIN heap 116.

If the value z is greater than the minimum value, the hole is in the "wrong" heap, and z needs to be put into the Min-heap 116 instead. This correction is made by moving a Min-heap 116 top or Max-heap 114 top from the heap not containing the oldest value into the location of the oldest sample. If the heap identified for the new sample is not the same as the heap identified for the oldest sample, the new sample is placed into the location of the Min-heap 116 top or Max-heap 114 top and moved from the heap not containing the oldest value. To create room in the Min-heap 116 for the new value z, the current minimum value from the Min-heap 116 is exchanged with the "hole" node, and the new value z is placed at the top of the Min-heap 116. At this point, the values in the "hole" node and the minimum (MIN) node satisfy the median filter properties, but may violate heap properties. Two additional procedures, FixMaxHeap( ) and FixMinHeap( ) are provided to fix the heap properties of the respective heaps. In lines 7 and 9, the respective fix-heap routines are called to restore heap order. The ELSE clause in line 8 handles the case when the location of the hole is in the "correct" heap for the incoming value z.

Lines 10-15 provide the complementary case when the "hole" is in the Min-heap 116. The process is identical for the Min-heap 116 case with min/max reversed. In line 16, the value of the new median is computed and returned.

Referring to Table 4, the main work is accomplished by the two subroutines FixMaxHeap( ) and FixMinHeap( ). Since the location of the "hole" is arbitrary, the new node z may violate heap property by being smaller than its children, or larger than its parents (in the Min-heap 116 case). Heap properties are corrected by rebalancing the Max-heap 114 so the Max-heap 114 top contains the highest value in the Max-heap 114 and rebalancing the Min-heap 116 so the Min-heap 116 top contains the lowest value in the Min-heap 116. The Fix-Heap routines move the node down or up in the heap to restore the heap integrity. For simplicity, only FixMaxHeap( ) is shown. FixMinHeap( ) is the complementary case and is identical in form to FixMaxHeap( ).

TABLE 4

| Line | Item |
|------|------|
|  | FIXMAXHEAP( i ) |
| 1 | idx := i |
| 2 | done := FALSE |
| 3 | WHILE done = FALSE DO |
| 4 | l := Left( idx ) |
| 5 | r := Right( idx ) |
| 6 | IF l <= n/2 and HEAP[ l ] > HEAP[ idx ] |
| 7 | THEN largest := l |
| 8 | ELSE largest := idx |
| 9 | IF r <= n/2 and HEAP[ r ] > HEAP[ largest ] |
| 10 | THEN largest := r |
| 11 | IF largest = idx |
| 12 | THEN done := TRUE |
| 13 | ELSE Swap( idx, largest ) |
| 14 | idx := largest |
| 15 | z = HEAP[ i ] |
| 16 | WHILE i > 0 and HEAP[ Parent( i ) ] < z DO |
| 17 | Swap( i, Parent( i ) ) |

TABLE 4-continued

| Line | Item |
| --- | --- |
| 18 | i := Parent( i ) |
| 19 | HEAP[ i ] := z |

At line 1, the value of the node is copied to a second index (idx). This is simply to save the original node index for the subsequent code in lines 15-16. Line 2 sets a Boolean used to terminate the subsequent loop. Recursion was eliminated to simplify the implementation using a simple stream processor. The WHILE loop in lines 3-14 implement a version of the standard "heapify" routine which insures that the node is larger than both its children. If not, contents of the node are swapped with the larger of the two children (line 13) and the loop repeated until the node is larger than both children, or the bottom of the heap is reached.

Lines 15-19 perform the "upward" integrity fix-up of the heap. This section insures that the specified node is less than/equal to its parent. If not, the node is exchanged with its parent and the loop repeated until either the node is less than its parent, or the top of the heap is reached. Note that if any nodes are exchanged in the WHILE loop of lines 3-14, then the WHILE loop of lines 16-18 will not be executed due to the nature of the heap. In other words, either "upward" or "downward" integrity may be violated by the insertion of the new node z, but not both.

FIGS. 5-18 show an embodiment of interaction among a First-In-First-Out (FIFO ARRAY 112) buffer, a Max-heap 114, and a Min-heap 116 during filtering to display the basic operation of the median filtering algorithm. For simplicity, the augmented "back pointer" information in the IDX array is omitted. Only the FIFO ARRAY 112 index and heap structures are shown. For these examples, an n=16 size median filter is shown.

Figure 5:
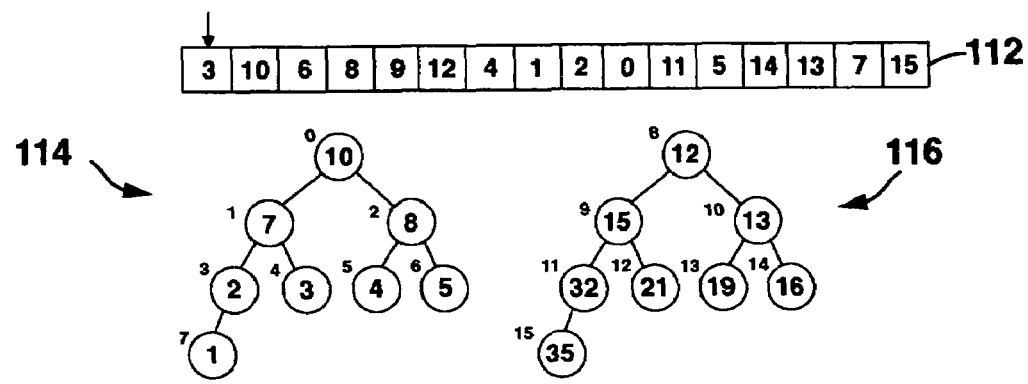
FIGS. 5-18 show an embodiment of interaction among a First-In-First-Out (FIFO) buffer, a Max-heap 114, and a MIN-heap during filtering.

FIG. 5 details the starting example configuration. At this point, the median filter is fully populated with sample data and the FIFO ARRAY 112 array contains pointer ordinals to individual HEAP array elements. The vertical arrow denotes the contents of the FIFO ARRAY 112 pointer inext. The active median value of the filter is 11=(10+12)/2.

Figure 6:
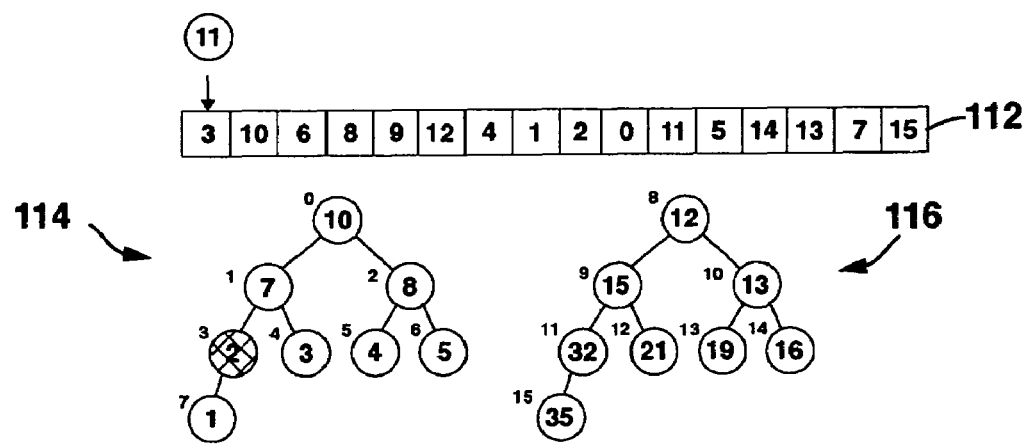

At FIG. 6, a new sample, z has been input with value 11. The FIFO ARRAY 112[inext] indicates the oldest sample in the array is at location 3, in the Min-heap 116 portion of the array.

Figure 7:
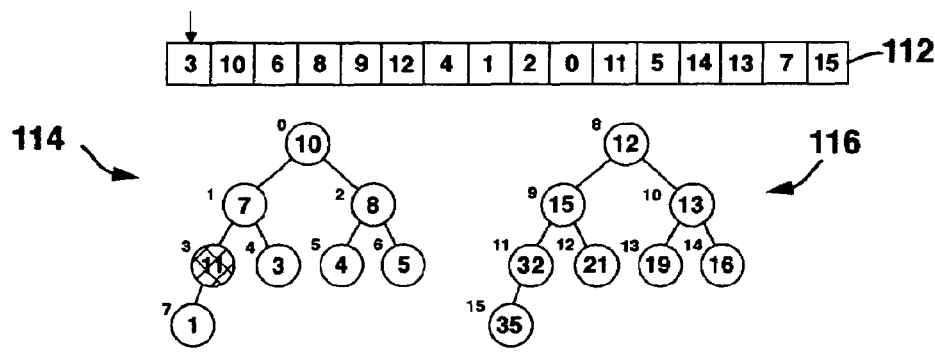

In FIG. 7, since the value of the new sample, z=11 is less than the Minimum value of the Min-heap 116, the "hole" is in the correct heap, and the value 11 is stored in the HEAP array at location 3.

Figure 8:
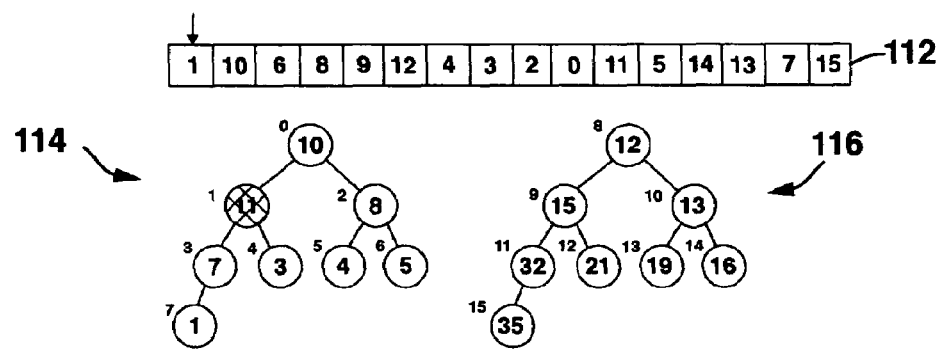
Figure 9:
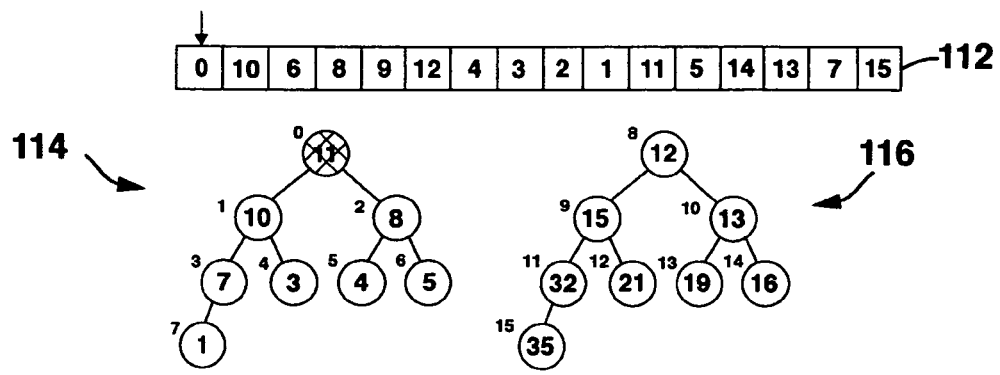

Since the new value, 11 violates the Min-heap 116 property, it must be moved "up" in the tree. In FIG. 8, the new value at node 3 is swapped with its parent. Note also, that the corresponding index values in the FIFO ARRAY 112 array have also been swapped, preserving the FIFO ARRAY 112 information.

The value of node 1 is still larger than its parent, so in FIG. 9, it is again swapped with its parent. Heap order has been restored, and the new median value is (11+12)/2. The value of inext is incremented and a new sample (22) is obtained.

Figure 10:
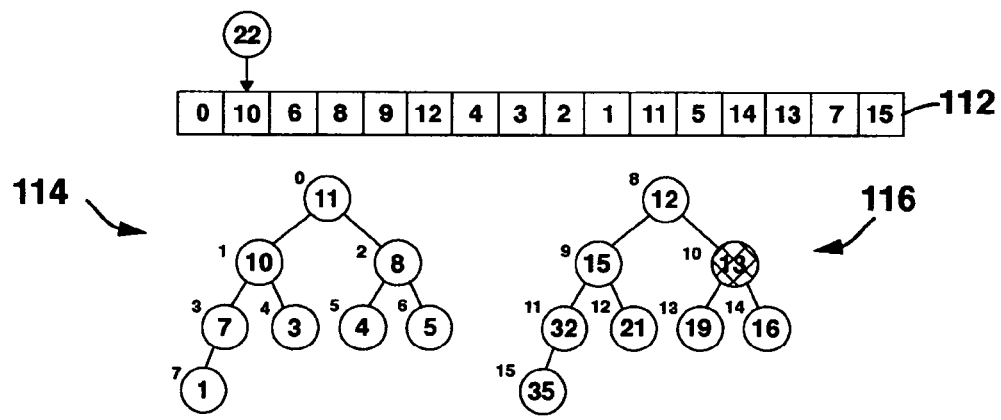

In FIG. 10, the index from FIFO ARRAY 112[inext] is 10, which is in the Min-heap 116, and the new value (22) belongs in the Min-heap 116.

Figure 11:
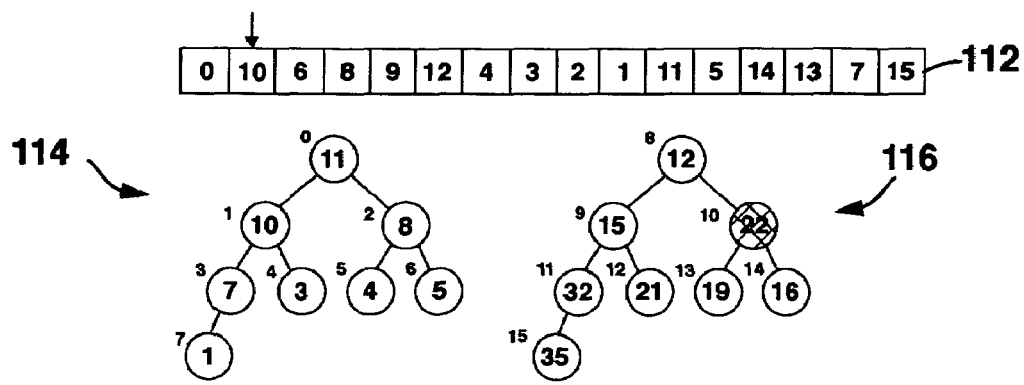

In FIG. 11, the new value (22) is inserted into the "hole" at location 10, but it violates the heap property by being larger than its children.

Figure 12:
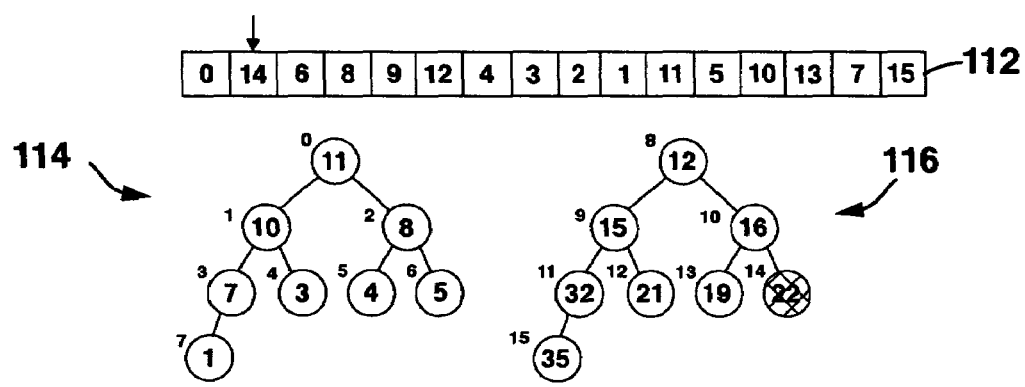

In FIG. 12, heap property is restored by swapping the new value (22) with the smaller of its children. Note again that the index information in the FIFO ARRAY 112 array reflects the changing indices of the swapped nodes.

Figure 13:
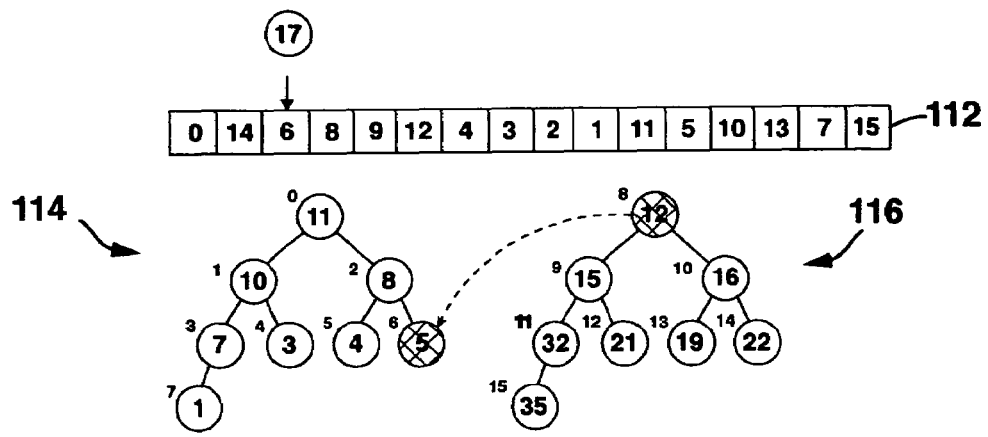

In FIG. 13, the value of inext has been incremented, and a new sample z=17 is obtained. The value at FIFO ARRAY 112[inext] is 6, indicating the hole is in the Min-heap 116. However, the new sample (17) needs to go into the Min-heap 116 to preserve the median filter property. At this point, the MINIMUM value of the Min-heap 116 needs to be moved to the node at index 6, and the new value moved to the node at index 8 (minimum(MIN)).

Figure 14:
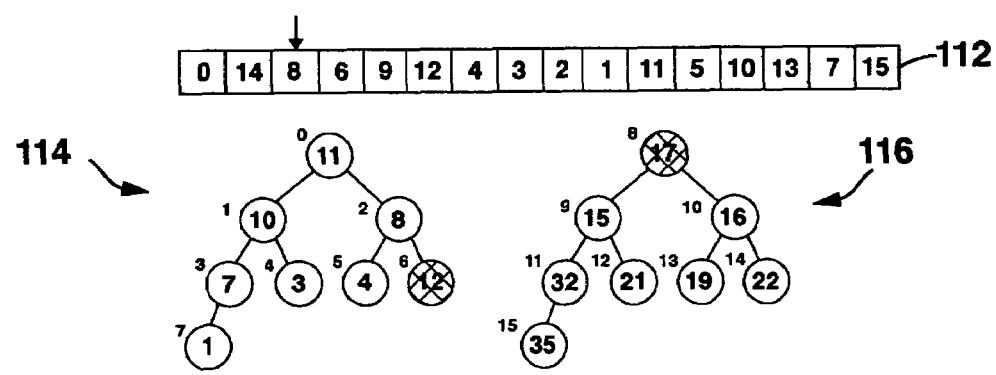

In FIG. 14, the previous minimum value from the Min-heap 116 has been moved to the "hole", and the new value (17) moved into the location occupied by the MIN value. Note again that FIFO ARRAY 112 reflects the new locations of the respective nodes.

Figure 15:
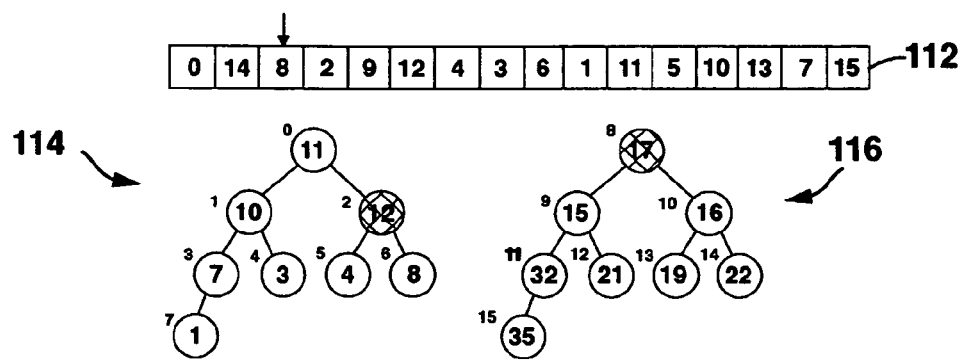

First, the Min-heap 116 is fixed up by moving the MIN node up to the top of the tree (FIG. 15).

Figure 16:
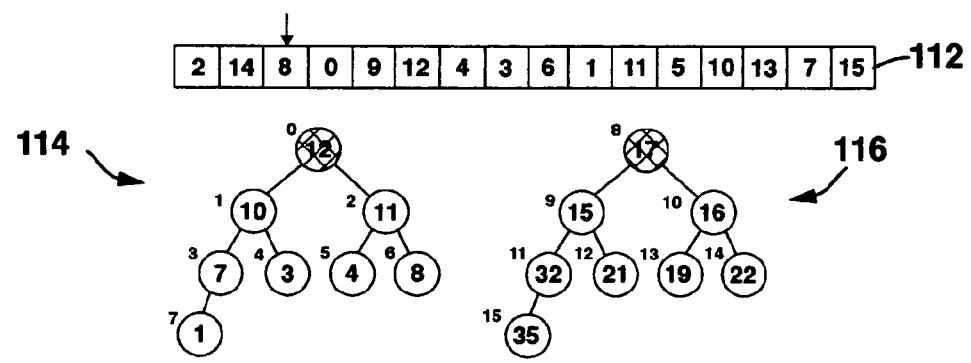

The old MIN node is now the MAX node of the Min-heap 116, but the Min-heap 116 still violates the Min-heap 116 property at the root. (FIG. 16).

Figure 17:
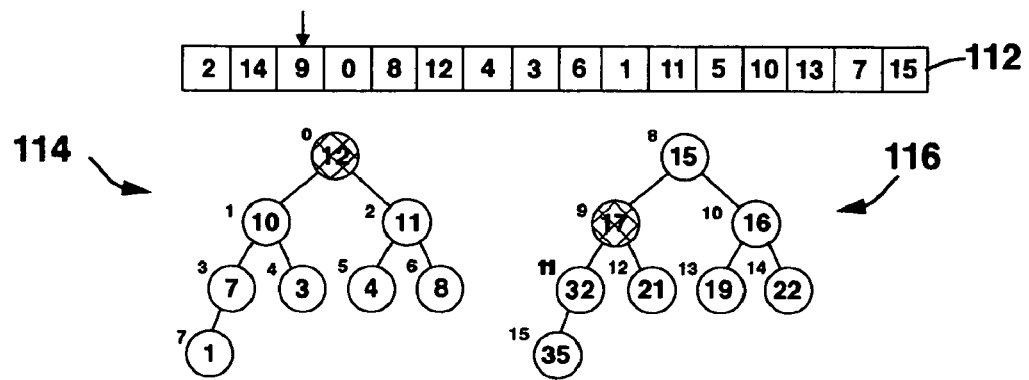

In FIG. 17, the new value (17) is swapped with the smallest child, and heap order is restored. The new median is (12+15)/2.

Figure 18:
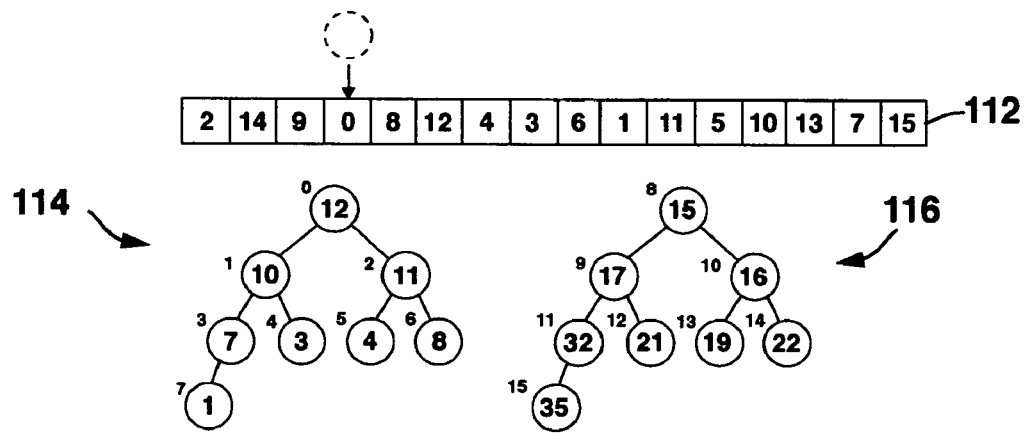

In FIG. 18, the structure is once again stable, inext has been incremented and we are ready for a new sample.

The median filter algorithm described in the preceding sections is attractive for use in a low-power device for several reasons. First, the algorithm runs in $O(2 \log n/2)$ time, with an average running time of $1.5(\log n/2)$ to calculate the median value where n is the total number of samples, and a measured running time less than that in a "typical" filtering application. Secondly, the algorithm utilizes binary heap structures in which "pointers" are simple array indices and can be computed using trivial computational mechanisms such as increment, add, and shift. This makes it ideal for implementation on simple/minimal hardware platforms. Thirdly, the median filter algorithm as proposed uses a small memory space (on the order of 3n) to represent structures, again a significant benefit for implementation on minimal hardware platforms.

The routine MedianFilter ( ) as described above, contains no loops, and runs from start to finish in one pass. The running-time for the MedianFilter routine itself is O(1). The bulk of time is spent in the FixMinHeap( ) and FixMax Heap( ) routines to restore heap order following the insertion of the "new" sample. Note that prior to any insertion, the heap is in correct heap order by definition. Following the insertion, the heap is either still in proper order, or violated in only one of two possible ways (for the Min-heap 116 side): new node is larger than its parent, and new node is smaller than one or both of its children. The new node cannot satisfy both case one and two. Therefore, either the first or the second WHILE loop in FixMaxHeap( ) will be performed, but not both.

The number of iterations that the WHILE loop in FixMaxHeap( ) runs is bounded by the height of the heap (log n). In the median filter, the total number of samples is divided into two equal-sized heaps of size n/2, therefore the worst-case running time for FixMaxHeap( ) (and FixMinHeap( ) accordingly) is $O(\log n/2)$. Since each execution of MedianFilter( ) can result in at most one call to FixMax- Heap( ) and one call to FixMinHeap( ), the total running time for the Median Filter Algorithm is O(2 log n/2).

The contents of the FIFO ARRAY 112 array contain an equal number of "pointers" to the MAX and Min-heap 116s respectively. Over some period of time, the order of these indices becomes random and unpredictable. However, in the mean, any arbitrary input value will result in one of exactly four cases. Hole in Min-heap 116, new sample in Min-heap 116. Hole in Min-heap 116, new sample in Min-heap 116. Hole in Min-heap 116, new sample in Min-heap 116. Hole in Min-heap 116, new sample in Min-heap 116. Cases 1 and 4 will result in only a single call to either FixMaxHeap( ) or FixMinHeap( ). Cases 2 and 3 will result in calls to both FixMaxHeap( ) and FixMinHeap( ). If we can assume that the index distribution in the FIFO ARRAY 112 array is random, there is an equally likely probability that any one of the four cases will be applicable. In half the cases, the running time will be bounded by log n/2, and in the other half, the bound is 2 log n/2, for an average running time of 1.5(log n/2).

Figure 19:
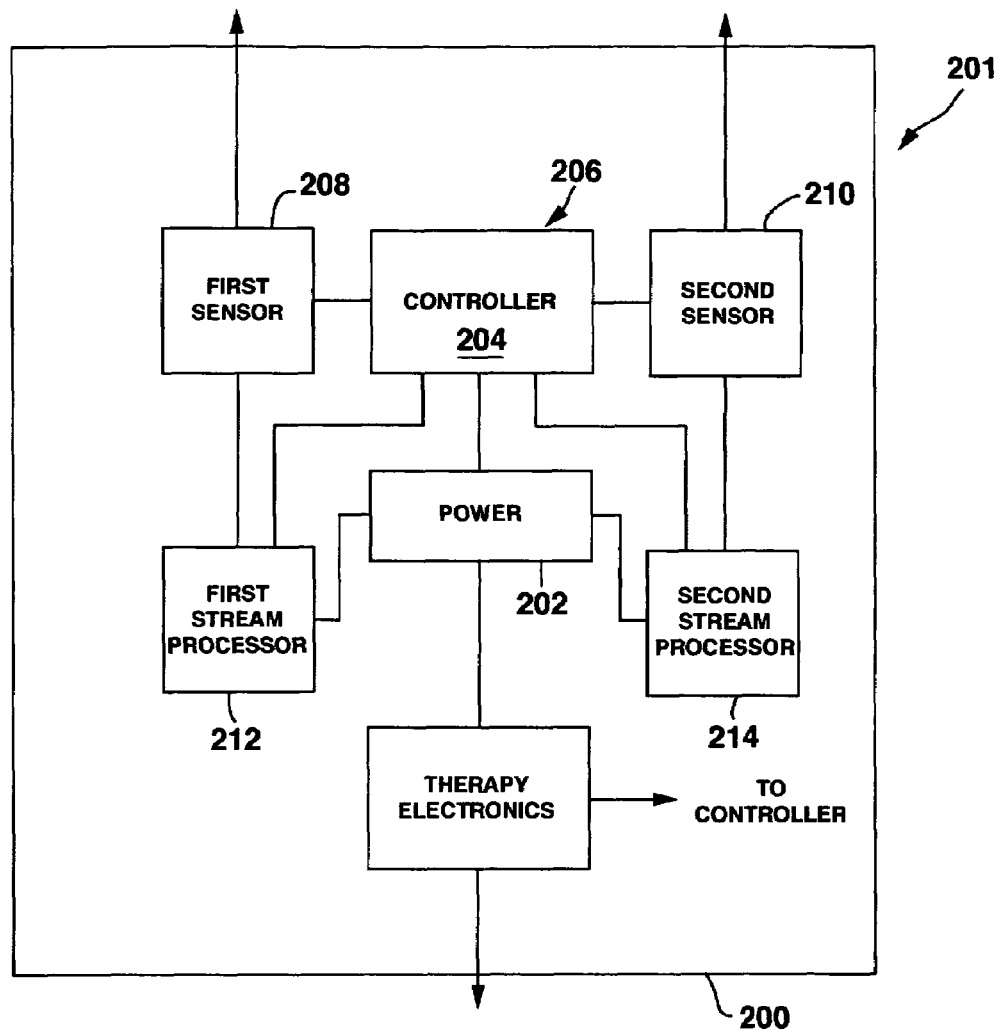
FIG. 19 shows a block diagram of a stream processor for an implantable medical device embodiment.
Figure 20:
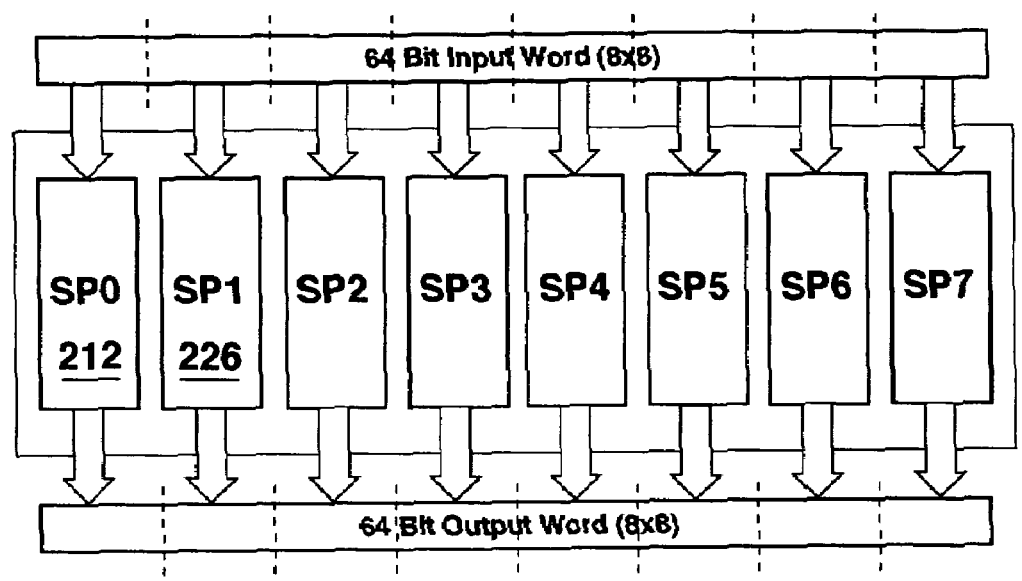
FIG. 20 shows a block diagram of a stream processor array for an implantable medical device embodiment.

FIG. 19 shows a block diagram of a stream processor for an implantable medical device embodiment, and FIG. 20 shows a block diagram of a stream processor array for an implantable medical device embodiment. The Implantable Stream Processor, in essence, is an array of several identical, simple microcontrollers (stream processors), each running identical kernel code. The ISP takes a large data word as input, and each individual stream processor executes a specified algorithm on a single byte of the larger data word. After each individual stream processor completes, the larger data word is reconstructed from the processed byte-output of the individual stream processors and made available for further processing by an external microprocessor.

FIG. 19 shows a block diagram of a stream processor array for an implantable medical device embodiment; FIG. 20 shows a block diagram of a stream processor array for an implantable medical device embodiment; FIG. 21 shows a detailed block diagram of a first stream processor embodiment; and FIG. 22 shows a detailed block diagram of a second stream processor embodiment. A general purpose implantable stream processor 201 comprises a housing 200; a power source 202 contained in the housing 200; a controller 204 coupled to the power source 202, the controller 204 having memory 206; a first physiological sensing apparatus 208 and at least a second physiological sensing apparatus 210 coupled to the controller 204. A first stream processing element 212 is coupled to the first physiological sensing apparatus 208. The first stream processing element 212 is also coupled to the power source 202 and the controller 204. The first stream processing element 212 can be configured to suspend operation once a first single digitized data input sample has been processed to conserve power and the second stream processing element 214 suspends operation once a second single digitized data input sample has been processed to conserve power. The first stream processing element 212 includes the following components. A first data input 215 is coupled to a first first-in first-out (FIFO) input buffer 216. The first data input 215 is coupleable to a first implantable physiological sensing apparatus 208. A first central processing unit (CPU) 218 is coupled to the first FIFO input buffer 216. A first local memory 220 configured for containing an executable program and first data is coupled to the CPU 218. A first output 222 is coupled to a first first-in first-out (FIFO) output buffer 224 and coupled to the first CPU 218. The first CPU 218 can be configured to suspend first stream processor 212 element operation once a first single digitized data input sample has been processed to conserve power and the second CPU 226 suspends second stream processor element 214 operation once a second single digitized data input sample has been processed to conserve power. The first CPU 218 has a single addressing mode for accessing the first local memory and the second CPU also has the single addressing mode for accessing the second local memory. The first CPU and the second CPU 226 contain a reduced instruction set for an implantable medical device. The executable program can include a median filtering algorithm. The first CPU 218 is configured for coupling to a supervising controller to control the first data input 215 and the first output 222 and the second CPU 226 is configured for coupling to the supervising controller 204 to control the second data input 228 and second output 230.

A second stream processing element 214 is coupled to the second physiological sensing apparatus 210. The second stream processing element 214 is also coupled to the power source 202 and the controller 204. The second stream processing element 214 includes the following elements that also correspond to the first stream process element 212. A second data input is coupled to a second first-in first-out (FIFO) input buffer. The second data input is coupleable to a second implantable physiological sensing apparatus. A second central processing unit (CPU) is coupled to the second FIFO input buffer. A second local memory is configured for containing the executable program and second data. The second local memory is coupled to the second CPU. A second output is coupled to a second first-in-first-out (FIFO) output buffer and coupled to the second CPU. In addition to the second stream process element, embodiments can include in number of additional stream process elements such as eight, sixteen, thirty-two, sixty-four.

The ISP consists of 8 independent stream processors (SP0-SP7). The 64 bit input data word is actually the digitized output of 8 independent analog-digital converters which are designed to sample 8 input channels in parallel at 250 Hz. Each individual stream processor takes its respective input byte, computes the median of the past 256 input samples, then outputs the result. When all 8 stream processors have completed, the aggregate results are presented to an output bus and made available for further processing by the controller.

FIGS. 21 and 22 contains the block diagram for each of the individual stream processors. Each stream processor ($SP_0$-$SP_7$) contains a 4 byte input FIFO, a 4 byte output FIFO, 1K bytes of static RAM, 256 bytes of ROM containing the Median Filter algorithm, and a simple 8-bit ALU. The processor has eight 8-bit general-purpose registers, a 16 bit program-counter, a single 16 bit base address register, a single 16-bit "stack", a very limited instruction set and a single (indexed) memory addressing mode.

One of the key aspects of this application/approach is the localization of the processing and data for each stream. Since each SP is operating on an independent data stream, no communication needs to occur between each SP. To minimize data contention issues between the SPs and the external bus, all communication to/from each stream processor occurs through the FIFO register queues. Instructions to read and write the respective FIFO queues are provided. Reads to an empty input FIFO queue result in suspension of processor activity until an external write to the queue occurs. This is a key mechanism in reducing the power consumption of the ISP as a whole. Data and Program Code occupy separate address spaces.

The major ISP design goals are speed, simplicity and power-reduction. Design simplicity leads to a reduction in overall transistor count and circuit complexity, thereby providing the IC area to replicate 8 stream processors on a single integrated circuit without increasing the power consumption of the device as a whole. Simplicity has been achieved through several mechanisms:

The overall architecture of each processor is built around a simple microprocessor with limited capability. The memory is organized as 8-bit words, and each of the 8 general-purpose registers is 8 bits in length. This reduces the number of flip-flops required to implement the design. Only three internal registers require 16 bits (program counter, address base register X, and a single word "stack"). Consistent with present designs, the processor does not utilized advanced features such as pipelining, which further simplifies the overall internal architecture.

The instruction set consists of 37 instructions, the majority of which occupy a single 8-bit opcode and execute in one or two clocks. 31 of the instructions are decoded from the upper 5 bits of the opcode, the remaining 3 bits specify a destination or target register. This approach yields a simple decode procedure and a compact code-set, reducing the amount of memory devoted to code space.

The processor employs eight 8-bit general purpose registers, 0-7. Register 0 always contains the value 0, so is not a "true" register. Registers 1 and 2 may be used in memory access instructions as index values to form the target address. Register 1 is used as an "accumulator" for certain operations.

In addition to the 8 general registers, a 16-bit Address Base Register (X) is used when addressing data memory, and a single 16-bit Address Save Register is used by the CALL instruction to provide a simple one-level call sequence. This limited register set reduces the overall complexity and component count.

Memory of 256 bytes of program ROM space is provided for each stream processor. This is an arbitrary number and was chosen to contain the target median filtering application only. Power consumption of ROM is minimal generally, but the desire to reduce die area results in a minimal ROM space.

Memory of 1K bytes of data are available in Static RAM. Although the target application requires only 778 bytes, 1K has been made available to support other algorithm methods in testing. Reduced memory results in smaller die size, and lower static and dynamic current consumption.

A Harvard architecture approach is employed which reduces the decode complexity for program code fetches vs. data access. All data memory access is via a single base-index addressing mode which results in simple memory address computation. Register 1 or 2 (depending on the specific instruction) are added to a 16 bit base address register (X), resulting in a target memory address from which individual 8-bit bytes are read/written.

As detailed earlier, all I/O occurs through a single input FIFO and a single output FIFO. No memory decoding is necessary.

Although the intended clock rate for the ISP is slow by "normal" standards, speed, in this case, is a desired outcome to provide the necessary performance for the filtering application at low clock rates.

Speed is achieved through the use of asynchronous logic techniques which reduce the clock transitions required per operation. This technique is employed in current implantable medical device processors and does not represent technological risk for future implementation. Most instructions execute in a single clock cycle, and the worst-case clocks-per-instruction is 5.

The final goal, power reduction, is achieved generally through the simplified architecture and execution speed (in combination with a reduced clock rate). One design element further reduces power consumption and is a key justification for the stream processor approach generally:

When an individual SP Reads from an empty FIFO queue, the processor is disabled until the queue becomes non-empty. Since the overall speed of the ISP is dictated by worst-case algorithm performance, but average performance will be much better, this technique results in significant "off-time" in which no dynamic current is being consumed.

Some embodiments of the implantable stream processor can include therapy electronics coupled to the power source and the controller and a therapy delivery element coupled to the therapy electronics. The therapy electronics can be electronics such as cardiac rhythm management electronics, cardiac monitoring electronics, neurological stimulation electronics, neurological monitoring electronics, and therapeutic substance delivery electronics. The therapy delivery element is selected from the group consisting of a cardiac lead and a neurological lead.

Thus, embodiments of the implantable medical device stream processor are disclosed to provide rapid computation using simple architecture and low power. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable medical device having a stream processor, comprising:
    a hermetically sealed housing;
    a power source;
    a controller in the housing, the controller coupled to the power source;
    a first physiological sensor;
    a first stream processing element coupled to the first physiological sensor, the first stream processing element also coupled to the controller.

2. The implantable medical device as in claim 1 further comprising: at least a second physiological sensor; and
    at least a second stream processing element coupled to the second physiological sensor, the second stream processing element also coupled to the controller.

3. The implantable medical device as in claim 1 further comprising therapy electronics coupled to the power source and the controller and a therapy delivery element coupled to the therapy electronics.

4. The implantable medical device as in claim 3 wherein the therapy electronics are selected from the group consisting of cardiac rhythm management electronics, cardiac monitoring electronics, neurological stimulation electronics neurological monitoring electronics, and therapeutic substance delivery electronics.

5. The implantable medical device as in claim 3 wherein the therapy delivery element is selected from the group consisting of a cardiac lead and a neurological lead.

6. The implantable medical device as in claim 3 wherein the first stream processing element suspends operation once a first single digitized data input sample has been processed to conserve power and the second stream processing element suspends operation once a second single digitized data input sample has been processed to conserve power.

7. An implantable medical device having a stream processor, comprising:
- a hermetically sealed housing;
- a power source;
- a controller contained in the housing, the controller coupled to the power source;
- a first physiological sensor;
- means for first stream processing coupled to the first physiological sensor, the means for first stream processing also coupled to controller.

8. The implantable medical device of claim 7 further comprising:
- a second physiological sensor; and
- means for second stream processing coupled to the second physiological sensor, the means for second stream processing also coupled to the controller.

9. An implantable stream processor comprising:
- a first stream processing element, comprising:
  - a first data input coupled to an input buffer, the first data input coupleable to a first implantable physiological sensor;
  - a first processing unit coupled to the first input buffer;
  - a first output coupled to an output buffer and coupled to the first processing units;
- a power source coupled to the first stream processing element; and
- an implantable housing which contains the power source.

10. The stream processor as in claim 9 further comprising a first local memory containing an executable program coupled to the processing unit.

11. A stream processor for an implantable medical device comprising:
- a first stream processing element, comprising:
  - a first data input coupled to an input buffer, the first data input coupleable to a first implantable physiological sensor;
  - a first processing unit coupled to the first input buffer; and
  - a first output coupled to an output buffer and coupled to the first processing unit; and
- at least a second stream processing element, the second stream processing element comprising:
  - a second data input coupled to a second input buffer, the second data input coupleable to a second implantable physiological sensor;
  - a second processing unit coupled to the second input buffer; and
  - a second output coupled to a second output buffer and coupled to the second processing unit.

12. The stream processor as in claim 11 wherein the first processing unit suspends first stream processor element operation once a first single digitized data input sample has been processed to conserve power and the second processing unit suspends second stream processor element operation once a second single digitized data input sample has been processed to conserve power.

13. The stream processor as in claim 11 wherein the first processing unit and the second processing unit contain a reduced instruction set for an implantable medical device.

14. A stream processor for an implantable medical device comprising:
- a first stream processing element, comprising:
  - a first data input coupled to an input buffer, the first data input coupleable to a first implantable physiological sensor;
  - a first processing unit coupled to the first input buffer; and
  - a first output coupled to an output buffer and coupled to the first processing unit; and
- a first local memory containing an executable program coupled to the processing unit,
- wherein the first processing unit has a single addressing mode for accessing the first local memory.

15. A stream processor for an implantable medical device comprising:
- a first stream processing element, comprising:
  - a first data input coupled to an input buffer, the first data input coupleable to a first implantable physiological sensor;
  - a first processing unit coupled to the first input buffer; and
  - a first output coupled to an output buffer and coupled to the first processing unit; and
- a first local memory containing an executable program coupled to the processing unit,
- wherein the executable program includes a median filtering algorithm.

16. A stream processor for an implantable medical device comprising:
- a first stream processing element, comprising:
  - a first data input coupled to an input buffer, the first data input coupleable to a first implantable physiological sensor;
  - a first processing unit coupled to the first input buffer; and
- a first output coupled to an output buffer and coupled to the first processing unit,
- wherein the processing unit is configured for coupling to a supervising controller to control the first data input and the first output.

17. A medical device comprising:
- a power source;
- a controller coupled to the power source;
- a first physiological sensor;
- a second physiological sensor;
- a third physiological sensor;
- a first stream processing element coupled to the first physiological sensor, the first stream processing element also coupled to the controller;
- a second stream processing coupled to the second physiological sensor, the second stream processing element also coupled to the controller; and
- a third stream processing clement coupled to the third physiological sensor, the third physiological stream processing element also coupled to the controller.

* * * * *